United States Patent [19]

Stocker et al.

[11] Patent Number: 5,348,869
[45] Date of Patent: Sep. 20, 1994

[54] PROCESS FOR PRODUCING TOCOPHEROLS WITH SPHEROPLASTS OF ALGAE

[75] Inventors: Achim Stocker, Zurich; Wolf D. Woggon, Benglen, both of Switzerland

[73] Assignee: Hoffmann-La Roche Inc., Nutley, N.J.

[21] Appl. No.: 908,762

[22] Filed: Jul. 1, 1992

Related U.S. Application Data

[63] Continuation of Ser. No. 466,360, filed as PCT/EP89/00890, Jul. 28, 1989, published as WO 90/01554, Feb. 22, 1990, abandoned.

[30] Foreign Application Priority Data

Aug. 2, 1988 [EP] European Pat. Off. ............ 810529.3

[51] Int. Cl.$^5$ .......................... C12P 17/06; C12N 1/12
[52] U.S. Cl. .................................. 435/125; 435/257.1
[58] Field of Search ............... 435/125, 117, 155, 156, 435/257, 252.1; 549/408

[56] References Cited

U.S. PATENT DOCUMENTS 4,582,919  4/1986  Barner et al. .................. 549/554
4,709,055  11/1987  Barner et al. .................. 549/215

FOREIGN PATENT DOCUMENTS 129252  12/1984  European Pat. Off. .

OTHER PUBLICATIONS

Bold et al, "Introduction to the Algae" pp. 34–96, 1985.
Whistance, G., et al., J. Biochem., 117, 593–600 (1970).
Soll, J., et al., Phytochemistry, 19, 215–288 (1980).
Ruggeri, et al., Appl. and Env. Microbiology, 50, No. 6, 1404–1408 (1985) Derwent abstract 85–001455/01.
Brock, T. D. "Biology of Microorganisms", 1984, pp. 34–35 and 644–645.
Henry et al., Biochem J., 1987, vol. 242, pp. 367–373.
Mullins et al., Biochem Soc. Trans, 1985; vol. 13, pp. 1242–1243.
Powls et al., Biochem J., vol. 104, pp. 240–260, 1967.
Botham et al, Biochem J., 1971, Vol. 124(2).
Dasilva, et al., Biochim. Biophys Acta, vol. 239(e), pp. 345–347, 1971.
Mayer et. al., In "Methods in Enzymology", vol. XVIII, Part C, Academic Press, 1971, pp. 267–273.

Primary Examiner—Irene Marx
Attorney, Agent, or Firm—George M. Gould; George W. Johnston; John P. Parise

[57] ABSTRACT

A novel process for producing tocopherols and their precursors is described.

7 Claims, No Drawings

PROCESS FOR PRODUCING TOCOPHEROLS WITH SPHEROPLASTS OF ALGAE

This application is a continuation of application Ser. No. 07/466,360, filed as PCT/EP89/00890, Jul. 28, 1989, published as WO 90/01554, Feb. 22, 1990, now abandoned.

The present invention relates to a process for producing tocopherols and related compounds. More particularly, the invention relates to a process for producing the compounds of the formula

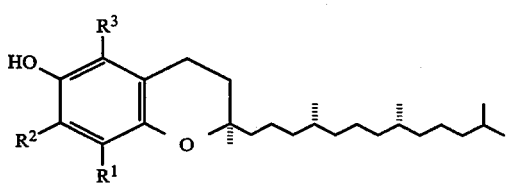

wherein $R^1$ is methyl and $R^2$ and $R^3$ are hydrogen, $R^1$ and $R^2$ are methyl and $R^3$ is hydrogen, $R^1$ and $R^3$ are methyl and $R^2$ is hydrogen or $R^1=R^2=R^3=$hydrogen or methyl
and the corresponding 3',7',11'-trienols, which process comprises treating the phytylbenzohydroquinone derivatives of the formula

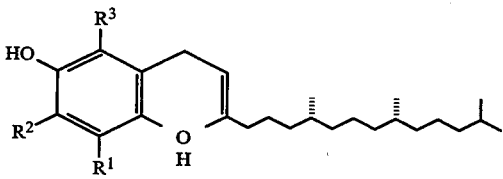

wherein $R^1$, $R^2$ and $R^3$ are as above, or the corresponding 2',6',10',14'-tetraen-yl hydroquinones, with (a culture of) spheroplasts of procaryotic blue-green algae (Cyanophyceae), or enzyme fractions obtained therefrom; the term (a culture of) is used to indicate that not only a culture, but also planctonic populations of the algae can be used.

The formula I encompasses the—preferred—(R,R,R)-α-tocopherol and the corresponding β,γ, and δ-tocopherols.

As is known, the following applies:

| | |
|---|---|
| $R^1=R^2=R^3=H$ | tocol |
| $R^1 = R^2 = R^3 = CH_3$ | α-tocopherol |
| $R^1 = R^3 = CH_3, R^2 = H$ | β-tocopherol |
| $R^3 = H, R^1 = R^2 = CH_3$ | γ-tocopherol |
| $R^2 = R^3 = H_3, R^1 = CH_3$ | δ-tocopherol |

In the foreground of the interest is R,R,R-α-tocopherol. The remaining compounds of the formula I as well as the trienols may primarily be considered to be precursors of R,R,R-α-tocopherol; see in this respect also U.S. Pat. No. 3,819,657 and U.S. Pat. No. 2,640,058 relating to the methylation of such precursors.

It has been known that in eucaryotic organisms such as in higher plants or green algae and in procaryotic blue-green algae the biosynthesis of tocopherols involves the condensation of homogentisates and phytyl pyrophosphates to form phytylbenzoquinol derivatives, which, by cyclisation and subsequent methylations, yield tocopherols. E.g., in Biochem. J. (1970) 117, 593–600 it is reported that in the higher plants Lactuca sativa and Rumex sanguineus, in the green algae Euglena gracilis and Chlorella pyrenoidosa and in the blue-green alga Anacystis nidulans homogentisates are biosynthetic precursors of plastoquinone, α-tocopherolquinone and the tocopherols. Moreover in Biochem. J. (1987) 242, 367–373 it is reported that the unicellular blue-green alga Scenedesmus obliquus contains α-tocopherol and different phytylbenzoquinone derivatives. Methylation of the aromatic ring at the precursor level as well at the tocopherol level has been shown to be mediated by SAM (S-adenosylmethionine), see Phytochemistry (1980) 19, 215–218.

However there is no evidence relating to the biosynthetic conversion of 5-phytyl-1,4-hydroquinone-precursors and 5-geranylgeranyl-1,4-benzohydroquinones into γ- and δ-tocotrienols respectively into tocopherols.

The process provided by the present invention now renders possible the production of tocopherols and tocotrienols from the corresponding benzoquinol derivatives by microorganisms.

An unexpected advantage of the present process consists in the fact that only the E derivatives II react, i.e. the Z isomers of the derivatives II do not react with the spheroplasts under consideration. In other words it is not necessary to use the starting materials II as 100% E isomers; mixtures of E derivatives II with their Z isomers can be used a starting materials.

Since the compounds II are more polar than the compounds I, the "unreacted" II can easily be separated, e.g. by way of chromatography.

The microorganisms used in the present invention are those belonging to the class of the procaryotic blue-green algae (Cyanophyceae). It is assumed that the cyclisation of the benzoquinol precursors to the tocopherols is catalysed by an up to now unknown enzyme which we call "tocopherol cyclase" due to its cyclising function. The tocopherol-cyclase activity may be determined by measuring the conversion of labelled or unlabelled benzoquinol derivatives respectively to labelled and unlabelled tocopherols respectively and tocotrienols by standard methods such as TLC-radioactivity-scanning, HPLC-radioactivity-monitoring and HPLC-fluorescence detection respectively.

The strains preferably used in the present invention are Anabaena variabilis (SAG 1403-4b) and Chlorogloeopsis (SAG 1411-1a). According to the classification in "Algen; Einführung in die Phykologie", 1984, ed. Christian van den Hoek, Georg Thieme Verlag Stuttgart, New York, Anabaena variabilis and Chlorogloeopsis are procaryonts of the class of Cyanobacteriae. The morphological and physiological characteristics of these strains are described in the mentioned manual. Any strain belonging to the above mentioned class, isolated from natural sources or publicly available from the usual collections, e.g. Sammlung yon Algenkulturen, Pflanzenphysiolog. Institut der Universität Göttingen (SAG), may be employed for the present invention.

The preferred strains are those containing tocopherol(s). Such content of tocopherol can easily be assayed by extracting a probe of the algae with, e.g. hexane, and then carry out a suitable gaschromatographic determination.

The process of this invention may be carried out by cultivating the microorganism in an appropriate medium in a known manner, and by using the modified form of the microorganism, namely spheroplasts of the organism, solubilized spheroplasts or enzyme fractions, in particular purified enzyme fractions.

It has been found that using spheroplasts in their unmodified form leads to substantial transport problems and thus lack of enzymatic activity.

Appropriate culture media are those conventional media containing carbon sources, nitrogen sources and those inorganic salts indispensable for the growth of the microorganism.

Carbon dioxide may serve as the carbon source but other substances, e.g. carbonates, may also be used. As nitrogen sources, there may be used inorganic salts such as nitrates or ammonium salts, etc. As the inorganic nutrients, for example, potassium phosphates, magnesium sulfate, ferrous and ferric chlorides, calcium chloride and the like may be employed.

There exist different methods for cultivating the above mentioned microorganisms. For example there may be used submerged cultures, such as shake flask cultures or fermentor cultures. Batch cultures or continuous cultures may be used.

Preferably the cultivation should be carried out under aerobic conditions. The cultivation should preferably be conducted in the presence of light at a pH of about 5.0 to about 9.0, preferably from about 6.5 to 8.0. A preferred temperature range for carrying out the cultivation is from about 20° C. to 37° C., preferably from 25° C. to 33° C. While the time for cultivation varies depending upon the particular microorganism and the medium to be used, about 4 to 10 days of cultivation usually yields the best results.

The process provided by the present invention is, as mentioned above, carried out by employing spheroplasts, solubilized spheroplasts (i.e. solubilized in aqueous media) or enzyme fractions of the cultivated microorganisms.

As it is known the term "spheroplast" refers to a spherical or near spherical structure of the cell as formed by the disruption or partial removal of the cell wall of a cell suspended in an isotonic (or hypertonic) medium.

The spheroplasts of the algae are obtained in the conventional manner, i.e. by the treatment of the intact cells with lysozymes [this term referring to a group of hydrolases which represent cell lysing enzymes]. This is conveniently done at a pH of about 6 to 8, in a temperature range of about 20° to 40° C., and for about 1 to 10 hours. The usual lysozyme preparations may be used, e.g. "Lysozym" as manufactured by Merck, Darmstadt. The appropriate dosage is about 15000–25000 units/g of the lysozyme preparation.

The preparation of the spheroplasts is conveniently effected in the presence of a hypertonic buffer, avoiding this way disruption of the cells.

The hypertonic buffer is by definition a buffer, having a higher osmotic pressure than that of the cells. This higher pressure can be achieved through the addition e.g. sucrose, see L. R. Semenova et al. Microbiologiya 51, 259 (1982).

The reaction of the spheroplasts with the chemical substrate.

In the case where spheroplasts are utilized, the benzoquinol derivatives II may be converted to the tocopherols in a hypertonic buffer under anaerobic conditions at a pH of about 6 to 8. Generally, cells from about 5 to 9 day cultures are preferred for obtaining the most effective cells for the formation of spheroplasts and thus for the conversion of the benzoquinol derivatives to tocopherols and tocotrienols.

In this conversion no additional nutrients are necessary.

On the other hand, when solubilized spheroplasts—this term referring to aqueous systems—or enzyme preparations are used, the conversion of the benzoquinol derivatives II to the tocopherols and tocotrienols may be carried out in commonly used non-hypertonic buffers under anaerobic conditions at a pH about 6 to 8. In this case, no nutrients need to be present.

In the case enzyme fractions are utilized, said enzyme fractions are conveniently obtained from solubilized spheroplasts by chromatography, e.g. ion exchange chromatography, liquid chromatography, gel filtration, gel electrophoresis, affinity chromatography, etc. One works conveniently in buffer solutions such as outlined above. The active fractions are determined by assay of the cyclase activity as outlined above. The necessary purification can be effected by detergents, preferably non-ionic detergents.

In each case a temperature range of ca. 25°–35° C. is feasible.

For the present reaction the substrates are preferably applied in a solution of a hydrophilic solvent, such as in acetone, methanol, ethanol, etc. or, in a solution containing such hydrophilic solvent.

Furthermore, the presence of a non-ionic detergent is preferred in order to maintain the activity of the enzyme.

Examples are: dodecyl-D-maltoside, Triton 100, Tween 80, etc.

The substrate may also be applied as a preformed complex, the advantages being:

1.) no hydrophilic co-solvent is needed [and thus the enzyme activity being easily maintained this way]
2.) the oxidation level of the substrate is easily maintained at the hydroquinone state in the presence of a reducing agent, e.g. an ascotbate, etc.
3.) the assay is homogenous, i.e. no formation of slurries does occur.

Suitable complexing agents are $\beta$-cyclodexrin, 2,6-di-O-methyl-$\beta$-cyclodextrin, etc.

The substrates I are preferably prevented from oxidation by the addition of reducing agent, such as $NaBH_4$, $Na_2S_2O_4$, ascorbates, etc.

The final concentration of the substrate for the conversion should be in a range of ca. 0.04 and 1 g/l with a reaction time depending on the microorganism. A reaction temperature of about 15° to 37° C., preferably of about 25° to 35° C. and a reaction time of about 2 to 20 hours usually brings the most preferable results.

A reasonable range of (solubilized) spheroplasts: compounds I would be ca. 10–20 g (centrifuged spheroplasts):$10^{-2} - 10^{-4}$ g.

The reaction mixture may be extracted and the products may be isolated from the extract by standard methods, such as chromatography and distillation, to give enantiomerically pure (R,R,R)-tocopherols and tocotrienols.

The following examples illustrate the present invention.

In these Examples, Substrate 1 is 2,3-dimethyl-5-[(E,7'R,11'R)-3',7'11'15'-tetramethyl-2'-hexadecenyl]-1,4-benzohydroquinone.

EXAMPLES

A. Composition of a suitable medium for the growth of the microorganisms

| Medium 1 | |
|---|---|
| MgSO$_4$.7H$_2$O | 0.150 g |
| K$_2$HPO$_4$ | 0.600 g |
| Ca(NO$_3$)$_2$.4H$_2$O | 0.010 g |
| KNO$_3$ | 0.500 g |
| Na-citrate.2H$_2$O | 0.165 g |
| Fe$_2$(SO$_4$)$_3$.6H$_2$O | 0.004 g |
| Solution A$_5$ | 1 ml |
| dist. water to | 1000 ml |
| Solution A$_5$: (trace elements) | |
| H$_3$BO$_3$ | 2.860 g |
| MnCl$_2$.4H$_2$O | 1.810 g |
| ZnSO$_4$.7H$_2$O | 0.222 g |
| MoO$_3$ | 0.015 g |
| CuSO$_4$.5H$_2$O | 0.079 g |
| dist. water to | 1000 ml |

B. Used microorganisms/substrate and suitable media

| Species/ colletion number | Optimal substrate conc. [mg/l] | Medium |
|---|---|---|
| Anabaena variabilis SAG B 1403-4b | 2–20 | 1 |
| Chlorogloeopsis SAG B 1411-1a | 2–20 | 1 |

C. Composition of suitable buffer solutions; in all cases based on phosphates.

| hypertonic buffer (pH 7) (for the production of spheroplasts) [buffer 1] | |
|---|---|
| Sucrose | 171.150 g |
| K$_2$HPO$_4$ | 3.483 g |
| KH$_2$PO$_4$ | 1.361 g |
| MgSO$_4$ . 7H$_2$O | 0.990 g |
| EDTA . 2Na | 0.065 g |
| dist. water to | 1000 ml |
| Hypertonic buffer (pH 7) (preparation of compounds I ex non-solubilized spheroplasts) [buffer 2] | |
| Substrate 1 | 0.100 g |
| Sucrose | 171.150 g |
| Ascorbate | 44.033 g |
| K$_2$HPO$_4$ | 3.483 g |
| KH$_2$PO$_4$ | 1.361 g |
| MgSO$_4$ . 7H$_2$O | 0.990 g |
| EDTA . 2Na | 0.065 g |
| 2,6-di-O-methyl-$\beta$-cyclodextrin | 6.000 g |
| dist. water to | 1000 ml |
| Buffer (pH 7) (preparation of solubilized spheroplasts) [buffer 3] | |
| K$_2$HPO$_4$ | 11.612 g |
| KH$_2$PO$_4$ | 4.536 g |
| Glycerol | 200.000 g (see C.C. Contaxis et al., Biochem. J.124, (1971), 623) |
| Dodecyl-D-maltoside | 6.639 g |
| 1,4-Dithio-D,L-threitol | 0.308 g |
| dist. water to | 1000 ml |
| Buffer (pH 7) (diluent for the preparation of compounds I ex solubilized spheroplasts) [buffer 4] (see P. Rosevear et al., Biochemistry 19, (1980), 4105 seq. | |
| K$_2$HPO$_4$ | 11.612 g |
| KH$_2$PO$_4$ | 4.536 g |
| dist. water to | 1000 ml |
| Buffer (pH 7) (for gel filtration) [buffer 5] | |
| K$_2$HPO$_4$ | 11.612 g |
| KH$_2$PO$_4$ | 4.536 g |
| Glycerol | 200.000 g |
| Dodecyl-D-maltoside | 0.511 g |
| 1,4-Dithio-D,L-threitol | 0.077 g |
| dist. water to | 1000 ml |

EXAMPLE 1

An agar slant culture of *Anabaena variabilis* SAG 1403-4b was inoculated in 100 ml medium 1 in a 200 ml-flask and cultivated at 31° C. for 6 days while bubbling medium 1 with a mixture of air/CO$_2$ (0.5% CO$_2$) under permanent illumination with 6 bulbs (Philips TLD 15W/33). After sedimentation for 10 minutes and decantation of the medium the residual culture was inoculated in 1.8 l of medium 1 in a 2 l-flask. Cultivation was carried out under the above mentioned conditions for 6 days. After sedimentation for 10 minutes and decantation of the medium the residual culture was inoculated in 8 l of medium 1 in a 10 l-flask.

When cultivated under the above mentioned conditions for 7 days, collecting cells by centrifugation at 1000 g yielded a sediment in the form of an pellet at a net weight of 3–3.5 g/l.

20 ml of buffer 1 (degassed) were transferred under argon to a 50 ml-flask containing 0.2 mg of the hydroquinone substrate 1, containing traces of the respective benzoquinone. Addition of 120 mg 2,6-di-O-methyl-$\beta$-cyclodextrin and stirring intensively at room temperature yielded a homogenous yellowish solution. Addition of 0.88 g ascorbic acid and gentle stirring for 3 hours yielded a homogenous colourless solution (buffer 2). The complete conversion of the benzoquinone in the substrate 1 to the hydroquinone could be measured by extracting 1 ml of buffer 2 with 1.5 ml of a mixture of hexane/methanol 2:1 and subjecting 0.02 ml of the overstanding hexane layer to HPLC-analysis.

Blue-green algae of 60 g net weight obtained by the above mentioned method were washed twice with 200 ml of buffer 1 and resuspended in a 500 ml-flask in 200 ml of buffer 1. The conversion of the cells to spheroplasts was carried out by adding 100 mg Lysozym (15000 E/mg, Merck) and slowly rotating the flask at 35° C. for 2 hours. The conversion to the spheroplasts was monitored by phase contrast microscopy every 20 minutes. The spheroplasts were collected by centrifugation at 4° C. and 1000 g for 5 minutes. After washing twice with 200 ml buffer 1 (degassed) at 4° C. under argon atmosphere the spheroplasts were maintained at 4° C. under argon until use.

20 g of spheroplasts were suspended under argon in a 100 ml-flask, containing 50 ml buffer 1 (degassed), at 4° C. and closed with a "pyrogallol" stopper (a wad of cotton-wool soaked with pyrogallol). After shaking the spheroplasts for 5 seconds with a vortex shaker, the enzyme reaction was started by the addition of 2 ml of buffer 2, containing 0.2 mg substrate 1, and additionally vortexing for 5 seconds. The flasks was incubated at 35° C. with a rotary shaker for 15 hours at 120 rpm. The amount of (2R,4'R,8'R)-$\gamma$-tocopherol accumulated was 0.186 mg (93%).

EXAMPLE 2

20 g of spheroplasts (Example 1) were suspended under argon in a 100 ml-flask, containing 10 ml buffer 3, at 4° C. and closed with a "pyrogallol" stopper. After slowly stirring for 1 hour at 4° C. solubilized spheroplasts were obtained and stored at 4° C. under argon until use.

40 ml of buffer 4 were added to 20 ml of solubilized spheroplasts under argon at 4° C. After vortexing the suspension for 30 seconds the enzyme reaction was started by the addition of 2 ml of buffer 2, containing 0.2 mg of the substrate 1 and additionally vortexing the suspension for 5 seconds. The flask was incubated at 35° C. with a rotary shaker for 15 hours at 120 rpm. The amount of the corresponding tocopherol accumulated was 0.136 mg (68%).

EXAMPLE 3

20 g of spheroplasts (Example 1) were suspended under argon in a 100 ml-flask, containing 50 ml buffer 1 (degassed), at 4° C. and closed with a pyrogallol stopper. After shaking the spheroplasts for 5 seconds with a vortex shaker, the enzyme reaction was started by the addition of 1.0 ml EtOH, containing 0.2 mg of the substrate 1 and 1 mg NaBH$_4$, and additionally vortexing for 5 seconds. The flask was incubated at 35° C. with a rotary shaker for 15 hours at 120 rpm. The amount of tocopherol accumulated was 0.070 mg (35%).

EXAMPLE 4

20 g of spheroplasts (Example 1) were suspended under argon in a 100 ml-flask, containing 50 ml buffer 1 (degassed), at 4° C. and closed with a pyrogallol stopper. After shaking the spheroplasts for 5 seconds with a vortex shaker, the enzyme reaction was started by the addition of 1.0 ml EtOH, containing 0.2 mg of the substrate 1, 50 mg 2,6-di-O-methyl-$\beta$-cyclodextrin and 1 mg NaBH$_4$, and additionally vortexing for 5 seconds. The flask was incubated at 35° C. with a rotary shaker for 15 hours at 120 rpm. The amount of tocopherol accumulated was 0.120 mg (60%).

EXAMPLE 5

For gel filtration (liquid exclusion chromatography (SEC)), a column (2.6×50 cm) was packed with Fractogel TSK HW65F (a polyethylene glycol dimethyl acrylate available from Merck) and equilibrated with 3 column volumes of buffer 5 at a constant flow of 2 ml/min./4° C. 20 ml of solubilized spheroplasts were centrifuged at 100,000 g/4° C. for 5 hours. The supernatant was separated from the sediment and subjected to gel filtration at 4° C. and a constant flow of 1 ml/min. The eluate was collected in fractions of 10 ml and assayed for cyclase activity according to by comparing with the similar experiment carried out in buffer 5. The cyclase was found to elute between 290 and 380 ml and highest activity was detected around 330 ml.

Analogous results were obtained with the remaining derivatives of formula II, namely with 3-methyl-5-[(E,7'R,11'R)-3',7'11'15'-tetramethyl-2'-hexadecenyl]-1,4-benzohydroquinone, leading to (2R,4'R,8'R)-δ-tocopherol, 2,3,6-trimethyl-5-[(E,7'R,11'R)-3',7'11'15'-tetramethyl-2'-hexadecenyl]-1,4-benzohydroquinone, leading to (2R,4'R,8'R)-α-tocopherol, 3-methyl-5-[(all E)-3',7',11',15'-tetramethyl-2',6',10',14'-hexadecatetraenyl] -1,4-benzohydroquinone, leading to (2R)-δ-tocotrienol, 2,3-dimethyl-5-[(all E)-3',7',11',15'-tetramethyl-2',6',10',14'-hexadecatetraenyl]-1,4-benzohydroqui-none, leading to (2R)-γ-tocotrienol, 2,3,6-trimethyl-5-[(all E)-3',7',11',15'-tetramethyl-2',6',10',14'-hexadecatetraenyl]-1,4-benzohydroquinone, leading to (2R)-α-tocotrienol, 2-[E,7'R,11'R)-3',7',11',15'-tetramethyl-2'-hexadecenyl]1,4-benzohydroquinone, leading to (2R)-tocol.

We claim:

1. A process for producing a compound of formula:

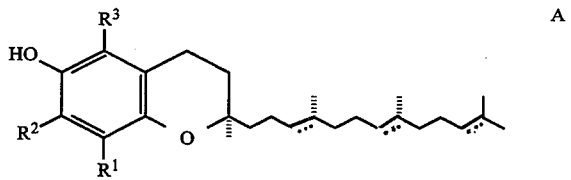

A wherein $R^1$ is methyl and $R^2$ and $R^3$ are hydrogen; $R^1$ and $R^2$ are methyl and $R^3$ is hydrogen; $R^1$ and $R^3$ are methyl and $R^2$ is hydrogen; or $R^1$, $R^2$ and $R^3$ are all hydrogen or all methyl, and ⁓ indicates a single or a double bond, with the proviso that all ⁓ within the compound must be the same, which process comprises:

(a) reacting a compound of formula

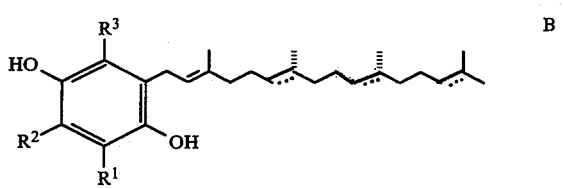

B wherein $R^1$, $R^2$, $R^3$ and ⁓ are respectively the same as in the compound of formula A, with β-cyclodextrin or 2,6-di-O-methyl-β-cyclodextrin to form a complex;

(b) treating the complex, in an effective amount of a reducing agent, with (i) spheroplasts of *Anabaena variabilis* SAG 1403-4b or *Chlorogloeopsis* SAG 1411-1, or (ii) spheroplasts of *Anabaena variabilis* SAG 1403-4b or *Chlorogloeopsis* SAG 1411-1 solubilized in a non-ionic detergent; and (c) recovering the compound of formula A.

2. A process according to claim 1, wherein said solubilized spheroplasts are used.

3. A process according to claim 1, wherein the concentration of the compound of formula B is 0.04 to 1 g/l.

4. A process according to claim 1, wherein in the compound of formula B $R^1$ and $R^2$ are methyl and $R^3$ is hydrogen.

5. A process according to claim 1, wherein in the compound of formula B $R^1$, $R^2$ and $R^3$ are all methyl.

6. A process according to claim 1, wherein spheroplasts of *Anabaena variabilis* SAG 1403-4b, or spheroplasts of *Anabaena variabilis* SAG 1403-4b solubilized in a non-ionic detergent are used.

7. A process according to claim 1, wherein spheroplasts of *Chlorogloeopsis* SAG 1411-1, or spheroplasts of *Chlorogloeopsis* SAG 1411-1 solubilized in a non-ionic detergent are used.

* * * * *